United States Patent [19]

Krauss et al.

[11] Patent Number: 5,113,848
[45] Date of Patent: May 19, 1992

[54] APPARATUS FOR SHOCK WAVE THERAPY

[75] Inventors: Werner Krauss, Knittlingen; Helmut Wurster, Oberderdingen; Thomas Belikan, Knittlingen, all of Fed. Rep. of Germany

[73] Assignee: Richard Wolf GmbH, Knittlingen, Fed. Rep. of Germany

[21] Appl. No.: 577,968

[22] Filed: Sep. 5, 1990

[30] Foreign Application Priority Data

Oct. 2, 1989 [DE] Fed. Rep. of Germany ....... 3932840

[51] Int. Cl.⁵ .............................................. A61B 17/22
[52] U.S. Cl. .................... 128/24 EL; 128/660.03
[58] Field of Search ............... 128/662.03, 660.03, 128/24 EL, 804; 269/322

[56] References Cited

U.S. PATENT DOCUMENTS 4,715,375 12/1987 Nowacki et al. ............ 128/24 EL
4,869,239 12/1989 Krauss et al. ............... 128/24 EL

FOREIGN PATENT DOCUMENTS 0084093  7/1983  European Pat. Off. .
0131654  1/1985  European Pat. Off. .
0226041  6/1987  European Pat. Off. .
0234366  9/1987  European Pat. Off. .
2351247  4/1975  Fed. Rep. of Germany .
3210919 10/1983  Fed. Rep. of Germany .
3220751 12/1983  Fed. Rep. of Germany .
3743883  7/1988  Fed. Rep. of Germany .
2192797  2/1974  France .
8703797  7/1987  PCT Int'l Appl. ............ 128/24 EL Primary Examiner—Ruth S. Smith
Attorney, Agent, or Firm—Panitch Schwarze Jacobs & Nadel

[57] ABSTRACT

Apparatus for shock wave therapy comprises an electroacoustic therapeutic transducer for generating ultrasonic shock waves, which are transmitted by way of a coupling medium shock wave transmission section of the transducer, bounded by a membrane, to the body of a patient reclining on a therapy table. In the interest of hygiene the membrane is releasably attached by its marginal area to the therapy table, being thereby exchangeable so that a new membrane can be provided for each patient. The extraction of gas from the coupling medium following exchange of the membrane is provided for.

15 Claims, 4 Drawing Sheets

APPARATUS FOR SHOCK WAVE THERAPY

FIELD OF THE INVENTION

The invention relates to a apparatus for shock wave therapy comprising an electroacustic therapeutic transducer for generating shock waves in the ultrasonic range, which are transmitted to the body of a patient to be treated by means of the shock waves, through a coupling medium shock wave transmission part of the transducer, bounded by an elastic membrane covering a porthole formed in a therapy table on which the patient reclines.

BACKGROUND OF THE INVENTION

There is disclosed in EP-A-0084093, a shock wave generator disposed in a bath filled with coupling medium, a patient reclining on a couch and being immersed in said bath so that the focus of the shock wave generator is directed on to a concretion in the patient, which concretion is to be disintegrated by means of the shock waves.

DE-A-2351247 discloses a shock wave generator located at one focal point of a focusing chamber in the form of part of an ellipsoid of revolution, said chamber being covered by an elastic membrane. By way of this membrane, the focusing chamber is applied to the patient's body, without the interposition of an air gap, in such a way that the concretion to be destroyed is positioned at the second focal point of the ellipsoid.

According to EP-A-0131654, alignment can be effected by axial displacement of the focusing chamber covered by a membrane, in a coupling cylinder which is applied to the patient's body and is likewise bounded by a membrane, a coupling medium being provided between the two membranes and within the focusing chamber itself.

DE-A-3220751 discloses the use of a shock wave generator comprising a flexible, coupling medium transmission part bounded by a film which is adaptable to the patient's body. Coupling is performed manually by the application of a coupling gel.

An object of the present invention is to provide improved apparatus for shock wave therapy in which the transmission of bacteria and pathogens is avoided, coupling of the shock waves to the patient's body being achieved simply, and with virtually loss-free transfer of acoustic radiation from said transmission part to the patient's body.

According to the invention the membrane is releasably attached at its marginal area to the therapy table, the membrane being thereby replaceable.

The membrane is thus a disposable article, a new membrane being provided for each patient.

The marginal area of the membrane may be pneumatically clamped to the therapy table. The membrane may be placed over a trough, surrounding the porthole in the therapy table, the trough being arranged to be connected to a vacuum source. Said trough may be formed on a ring in the form of an upwardly projecting pad surrounding and defining the porthole. The membrane may comprise a ready-made section of film, or a web of film comprising a series of such sections and which can be moved a section at a time across the porthole. The membrane preferably has a thickness of the order of 50 to 500 μm.

For low-loss coupling of the therapeutic transducer to the patient's body any gas which may collect in the transmission part when the membrane is changed must be removed. The gas may be removed by means of a device which operates beneath the membrane and within the transmission part to extract gas therefrom. Recesses may be machined into the upper marginal area of the part of the therapy table surrounding the porthole, so that gas in said transmission part can be extracted by way of the recesses, or an annular pipe having perforations in its inwardly and upwardly facing surface may be provided for extracting the gas. When using such gas extraction means, the membrane must be distended so that gas extraction takes place at the highest point of the membrane, at which gas bubbles collect.

Another means for extracting the gas comprises a tube which is extensible from the center of the therapeutic transducer, and which has a perforated extractor head at its tip. By extension of that tube the membrane undergoes a pyramid-shaped distortion, so that any gas bubbles which may be present in said transmission part make their way to the perforated extractor head located at the highest point that is to say at the apex of the pyramid. Such an effect can also be attained by the provision of a cranked extractor tube opening radially into said transmission part, and having a perforated extractor head at its free end, the extractor tube being rotatable about a radially guided part thereof. The extraction means described above are not, however, needed if the membrane is made of a material which is microporous and gas-permeable, but is impervious to water, being of polyurethane for example.

Figure 1:
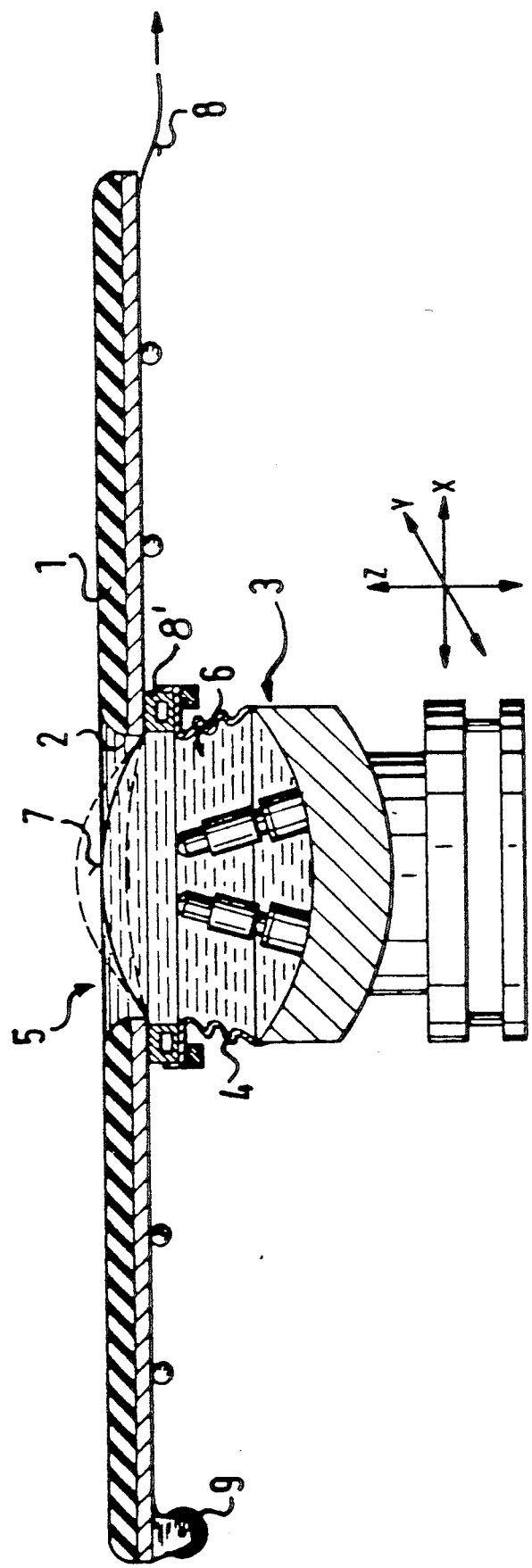
FIG. 1 is a diagrammatic side view shown partly in section of apparatus for shock wave therapy, according to a first embodiment of the invention.

As best be seen in FIG. 1, apparatus for shock wave therapy comprises a therapy table 1 for receiving a reclining patient and which has therein a porthole 2 of preferably circular cross-section. A focusing therapeutic transducer 3 for generating shock waves in the ultrasonic range, is arranged under the porthole 2 for positioning along three axes, X, Y and Z, relative to the therapy table 1. The transducer 3 is connected to the underside of the therapy table 1 by means of a flexible casing 4, which encloses the shock wave source of the therapeutic transducer 3, and is attached to the peripheral area of the port-hole 2 in (i.e. tightly sealed) fashion. A receptacle is thereby provided which when filled with a coupling medium 6, for example, water, constitutes a transmission part 5 for conducting shock waves generated by the therapeutic transducer 3 to the patient's body. In order to avoid contact between the patient's body and the coupling medium 6, the transmission part 5 is covered by an elastic membrane 7 in the region of the porthole 2, the membrane 7 also being connected to the casing 4 in tightly sealed fashion.

According to the embodiment shown in FIG. 1, the membrane 7 is provided by a web 8 in the form of a film drawn from a feed roll 9 along the underside of the therapy table 1 and over the porthole 2. The web 8 is passed between the underside of the therapy table 1 and a clamping ring 8' arranged to be pressed against the table 1. The clamping ring 8' is releasable for exchanging the membrane 7, by advancing the web 8 to allow an unused section thereof to be clamped in place by means of the clamping ring 8'. The extraction of any gas bubbles that may be present in the transmission part 5, which is necessary for its proper functioning is described below.

Figure 2:
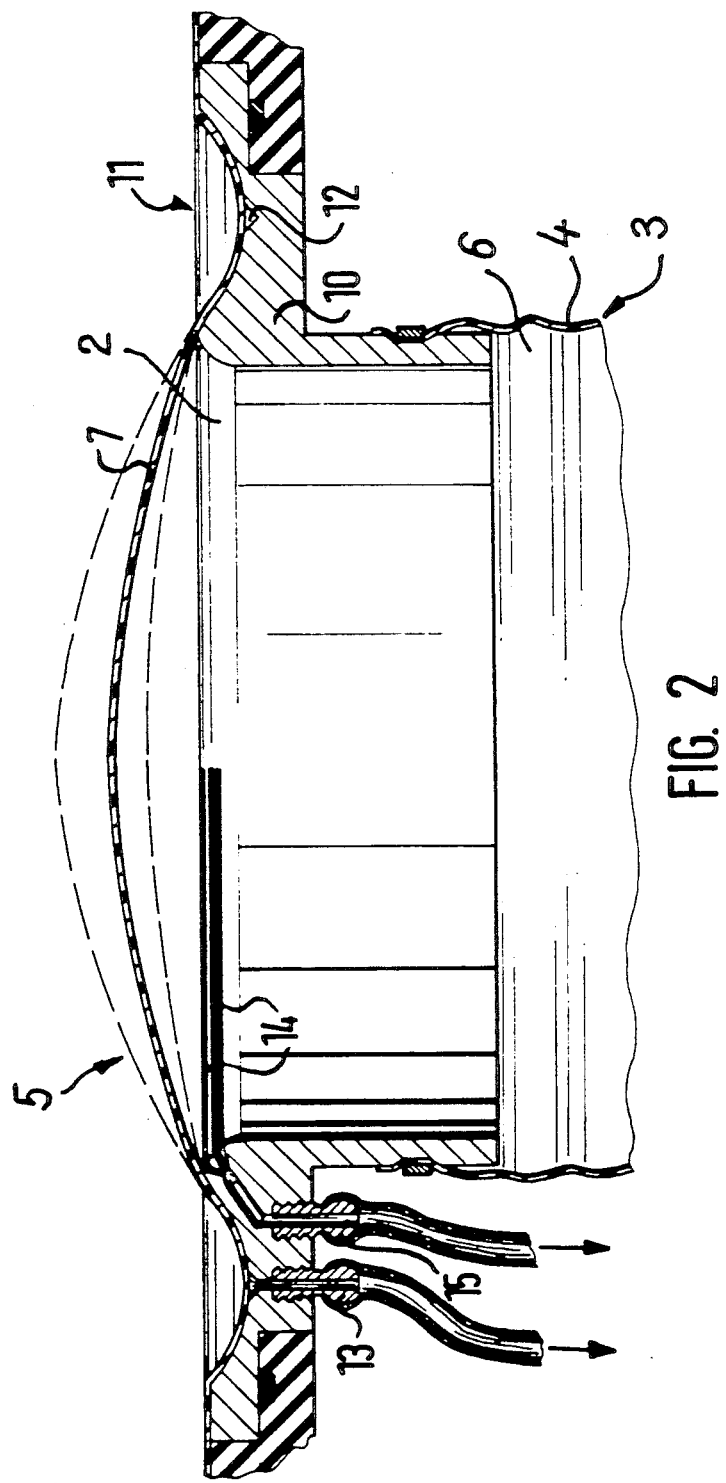
FIG. 2 is a diagrammatic fragmentary sectional view of apparatus for shock wave therapy, according to a second embodiment of the invention.

As shown in FIG. 2 a membrane 7 for bounding the transmission part 5 comprises a ready-made section of film which is pneumatically clamped between the upper end of the transducer 3 and the peripheral area of the porthole 2 in the therapy table 1, by a ring element 10. The element 10 extends upwardly from the coupling medium 6 and flexible casing 4 to the height of the upper surface of the therapy table and widens out defining a pad which surrounds and defines the porthole 2. The ring element 10 has a trough 11 the bottom of which is formed with an annular groove 12 connected by way of a hose connection 13 to a vacuum source (not shown). Evacuation of the annular groove 12 causes the membrane to be sucked down into the trough 11 and held fast therein in fluid-tight fashion. The membrane can easily be released again by turning off the vacuum. Any gas bubbles trapped in the coupling medium can be extracted through slots 14 in the upper part of the ring element 10 by means of an extraction hose 15 communicating with the slots 14, by causing the membrane 7 to distend downwards.

Figure 3:
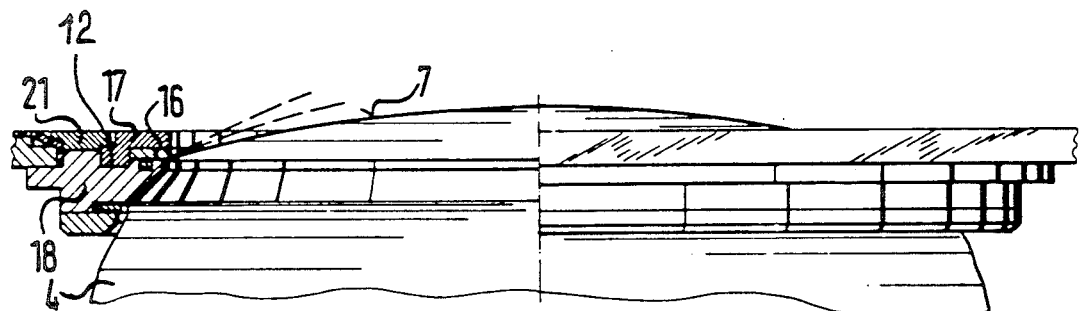
FIG. 3 is a diagrammatic side view shown partly in section of the upper part of apparatus for shock wave therapy, according to a third embodiment of the invention.
Figure 4:
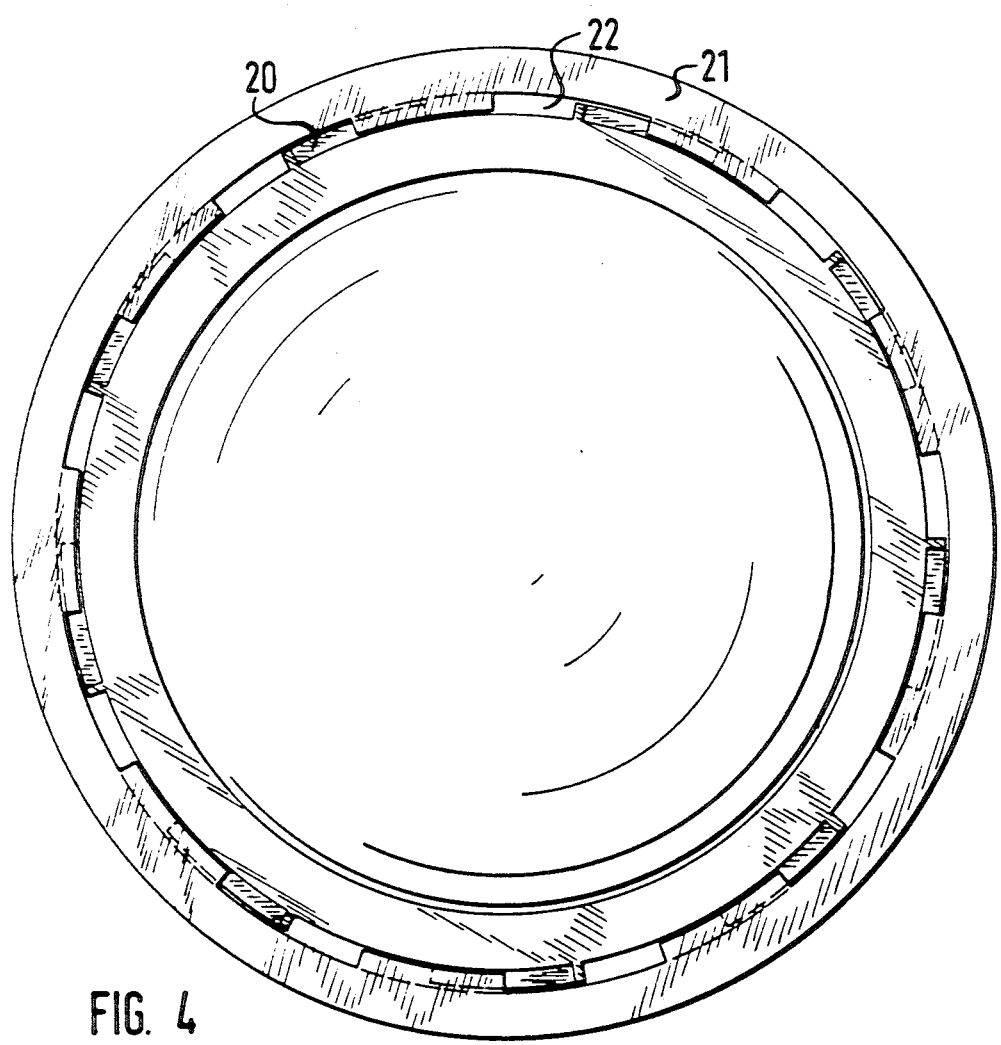
FIG. 4 is a top plan view of the embodiment of FIG. 3.

Another embodiment of the invention is shown in FIGS. 3 and 4. In this embodiment the membrane 7 is fastened at a ring 16 which can be clamped between a bayonet ring 17 and a support ring 18. After initially removing the bayonet ring 17 with its ring 16, the periphery of the membrane 7 is laid in a recess in the support ring 18. The ring 16 and the bayonet ring 17 are placed thereover, with tooth elements 12 on the periphery of the ring 17 engaging in matching recesses 22 in a retaining ring 21 surrounding the porthole 2 (FIG. 4). The bayonet is axially tightened by twisting it into place.

Figure 5:
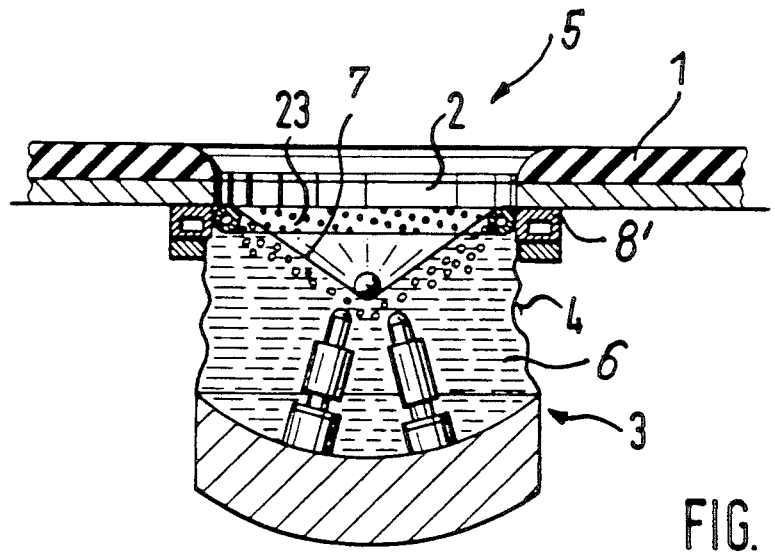
FIG. 5 to 7 are diagrammatic sectional views of apparatus for shock wave therapy, according to fourth, fifth and sixth embodiments of the invention, respectively.

The coupling medium may be degassed in various ways. For example as shown in FIG. 5, a circular pipe 23 may be provided, surrounding the upper peripheral area of the porthole 2, the pipe 23 having perforations in its inwardly and upwardly facing surfaces, and having means for connecting it to a vacuum source. For extracting gas bubbles from the coupling medium the membrane 7 may, for example, be made to distend downwards by weighting it at its center, so that the gas bubbles rise up to the pipe 23, which is the highest level in the transmission part 5, when the membrane 7 is so distended.

Figure 6:
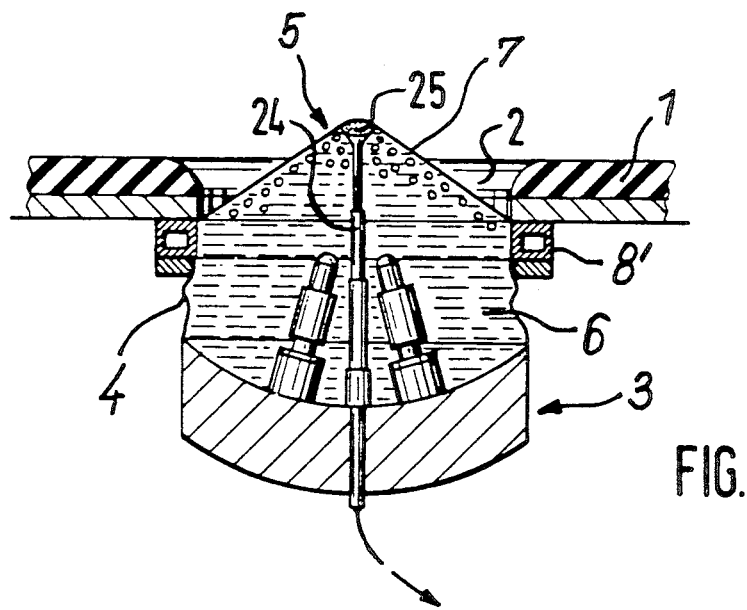

In the embodiment shown in FIG. 6, an extensible tube 24 capable of being extended from the center of the shock wave source of the therapeutic transducer 3, is provided at its tip with a perforated extractor head 25. By extending the tube 24 its extractor head 25 can be brought into contact with the membrane 7 thereby distending it upwardly so that gas bubbles in the coupling medium collect at the extractor head 25, from which they can be extracted.

Figure 7:
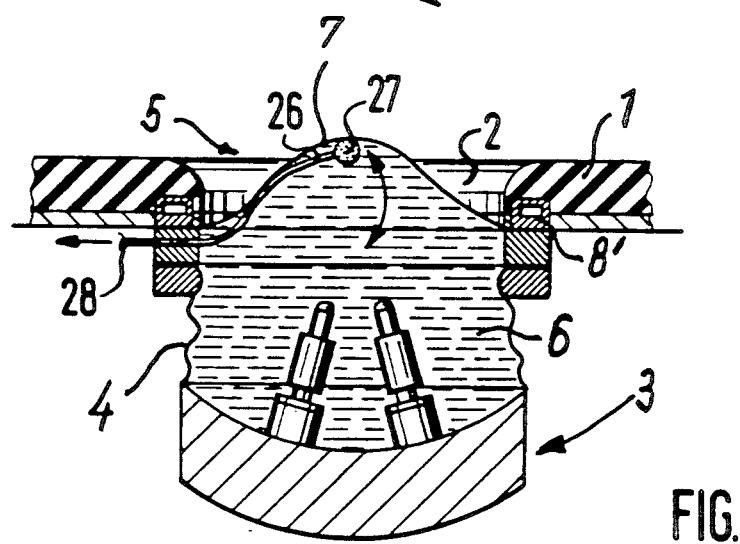

According to FIG. 7, a degassing device comprises a cranked extractor tube 26, opening radially into the transmission part 5, and being provided with a perforated extractor head 27 at its free end. The extractor tube 26 can be turned through 90° about a radial guided part 28 thereof, so that the extractor head 27 can be brought from a lateral position just below the undistended membrane 7 into a position in which the membrane 7 is distended upwardly as shown in FIG. 7.

For initially fixing the membranes 7 when in the form of ready-made sections of film, as described above with reference to FIGS. 2 to 7, before they are finally fixed in place by the means described above, the margins of these membranes may be provided with a self-adhesive coating.

In the embodiments described above the thickness of the membrane 7 is preferably of the order of 50 to 500 μm.

As another means for extracting gas from said coupling medium, the membrane may be microporous so that it is gas permeable but is water impervious, the membrane being made, for example, of polyurethane.

What is claimed is:

1. Apparatus for shock wave therapy, comprising:
    an electroacoustic therapeutic transducer for generating shock waves in the ultrasonic range;
    a therapy table for receiving a reclining patient to be treated by means of said shock waves, said table being formed with a porthole therethrough;
    an elastic membrane covering said porthole and having a marginal area surrounding the porthole;
    a coupling medium shock wave transmission means located for transmitting shock waves from the transducer to said patient by way of said membrane; and
    clamping means for releasably attaching the marginal area of the membrane to said therapy table.

2. Apparatus as claimed in claim 1, wherein said clamping means comprises means for pneumatically clamping said marginal area to said therapy table.

3. Apparatus as claimed in claim 1, wherein said clamping means comprises a trough surrounding said porthole and receiving said marginal area of said elastic membrane, and means for connecting a vacuum source to said trough to evacuate air from between said marginal area of said membrane and said trough.

4. Apparatus as claimed in claim 3, comprising an upwardly projecting pad surrounding said porthole, said trough being provided in said pad.

5. Apparatus as claimed in claim 1, wherein said membrane has a reinforced marginal rim in the marginal area of the membrane, and wherein the clamping means comprises a supporting ring and a bayonet ring, and mating bayonet coupling means on the support ring and the bayonet ring for releasably coupling said support ring and said bayonet ring together with said reinforced marginal rim clamped between said rings.

6. Apparatus as claimed in claim 1, wherein said membrane is a ready-made section of film.

7. Apparatus as claimed in claim 1, wherein said membrane is a section of a continuous web of film comprising a series of such sections, means being provided for feeding said web of film section by section across said porthole between said porthole and said transducer.

8. Apparatus as claimed in claim 1, wherein the thickness of said membrane is of the order of 50 to 500 μm.

9. Apparatus as claimed in claim 1, comprising a means operable beneath said membrane for extracting gas from beneath said membrane.

10. Apparatus as claimed in claim 9, wherein an upper peripheral area of said porthole is provided with recesses for the extraction therethrough of said gas.

11. Apparatus as claimed in claim 9, wherein said extracting means comprises an annular pipe surrounding the upper peripheral area of said porthole, and having perforations provided in inwardly and upwardly facing surfaces thereof.

12. Apparatus as claimed in claim 9, wherein said extracting means comprises a tube which is extensible from the centre of said transducer, towards said membrane said tube having a tip provided with a perforated, gas extractor head.

13. Apparatus as claimed in claim 9, wherein said extracting means comprises micropores in said membrane, said membrane being thereby gas permeable but water impervious.

14. Apparatus as claimed in claim 13, wherein said membrane is made of polyurethane.

15. Apparatus for shock wave therapy, comprising:
an electroacoustic therapeutic transducer for generating shock waves in the ultrasonic range;
a therapy table for receiving a reclining patient to be treated by means of said shock waves, said table being formed with a porthole therethrough;
an elastic membrane covering said porthole and having a marginal area surrounding the porthole;
a coupling medium shock wave transmission means located for transmitting shock waves from the transducer to said patient by way of said membrane;
clamping means for releasably attaching the marginal area of the membrane to said therapy table;
means operable beneath the membrane for extracting gas from between the membrane and the transmission means, the extracting means comprising a cranked extractor tube opening radially into said transmission means, a free end of said tube being provided with a perforated extractor head, and said tube having a radially guided part about which said tube is rotatable.

* * * * *